United States Patent
Jafari et al.

(10) Patent No.: US 7,820,194 B2
(45) Date of Patent: *Oct. 26, 2010

(54) COMBINATIONS OF VISCOELASTICS FOR USE DURING SURGERY

(75) Inventors: Masoud R. Jafari, Arlington, TX (US); Kerry L. Markwardt, Burleson, TX (US); Uday Doshi, Randolph, NJ (US)

(73) Assignee: Alcon, Inc., Hunenberg (CH)

( * ) Notice: Subject to any disclaimer, the term of this patent is extended or adjusted under 35 U.S.C. 154(b) by 1266 days.

This patent is subject to a terminal disclaimer.

(21) Appl. No.: 10/955,084

(22) Filed: Sep. 30, 2004

(65) Prior Publication Data

US 2005/0234012 A1 Oct. 20, 2005

Related U.S. Application Data

(63) Continuation-in-part of application No. 10/381,861, filed as application No. PCT/US02/36548 on Nov. 13, 2002, now abandoned.

(60) Provisional application No. 60/342,918, filed on Dec. 21, 2001, now abandoned.

(51) Int. Cl.
  A61F 2/00     (2006.01)
  A61F 13/00    (2006.01)
  A61K 31/795   (2006.01)

(52) U.S. Cl. .................. 424/427; 424/428; 424/422; 424/423; 424/78.35

(58) Field of Classification Search .......... 424/78.35, 424/423, 422
See application file for complete search history.

(56) References Cited

U.S. PATENT DOCUMENTS

| | | | |
|---|---|---|---|
| 4,141,973 A | 2/1979 | Balazs | |
| 4,486,416 A | 12/1984 | Soll et al. | |
| 4,920,104 A | 4/1990 | DeVore et al. | |
| 4,971,955 A * | 11/1990 | Soll et al. | 514/54 |
| 5,166,331 A | 11/1992 | della Valle et al. | |
| 5,273,056 A * | 12/1993 | McLaughlin et al. | 128/898 |
| 5,290,552 A | 3/1994 | Sierra et al. | |
| 5,409,904 A | 4/1995 | Hecht et al. | |
| 5,422,376 A | 6/1995 | Webb | |
| 5,492,936 A * | 2/1996 | Francese et al. | 514/772 |
| 5,498,606 A | 3/1996 | Soll et al. | |
| 5,501,706 A | 3/1996 | Arenberg | |

(Continued)

FOREIGN PATENT DOCUMENTS

EP     0 136 782    *  4/1985

(Continued)

OTHER PUBLICATIONS

Nishimura et al. ("Role of chondroitin sulfate-hyaluroniuc interactions in the viscoelastic properties of extracellular matrices and fluids," in Biochemica et Biophysica Acta, 1380 (1998) 1-9).*

(Continued)

*Primary Examiner*—Blessing M Fubara
(74) *Attorney, Agent, or Firm*—Mark E. Flanigan

(57) ABSTRACT

An improved viscoelastic composition useful in the performance of ophthalmic surgical procedures and especially cataract procedures is disclosed. The embodiments of the composition comprise combinations of sodium hyaluronate and chondroitin sulfate and exhibit an improved rheological profile.

13 Claims, 3 Drawing Sheets

U.S. PATENT DOCUMENTS

| | | | |
|---|---|---|---|
| 5,627,162 | A | 5/1997 | Gwon et al. |
| 5,792,103 | A | 8/1998 | Schwartz et al. |
| 5,811,453 | A | 9/1998 | Yanni et al. |
| 5,814,621 | A * | 9/1998 | Kanaya et al. ............ 514/54 |
| 5,929,050 | A | 7/1999 | Petito |
| 5,972,326 | A | 10/1999 | Galin et al. |
| 6,051,560 | A | 4/2000 | Chang et al. |
| 6,086,597 | A | 7/2000 | Fergeus et al. |
| 6,632,423 | B2 | 10/2003 | Doshi et al. |
| 6,906,044 | B2 | 6/2005 | Hermida Ochoa |

FOREIGN PATENT DOCUMENTS

| | | |
|---|---|---|
| EP | 0 214 853 A2 | 3/1987 |
| EP | 0 341 007 A2 | 11/1989 |
| EP | 0 781 547 B1 | 7/1997 |
| WO | WO 93/25187 A | 12/1993 |
| WO | WO 94/25004 | 11/1994 |
| WO | WO 97/41899 | 11/1997 |
| WO | WO 98/26777 | 6/1998 |
| WO | WO 98/41171 | 9/1998 |
| WO | WO 99/24070 | 5/1999 |
| WO | WO 01/68079 A2 | 9/2001 |
| WO | WO 02/40056 A2 | 5/2002 |

OTHER PUBLICATIONS

Nishimura et al. ("Role of chondroitin sulfate-hyaluronan interactions in the viscoelastic properties of extracellular matrices and fluids," in Biochemica et Biophysica Acta, 1380 (1998) 1-9).*

Adams, "Viscosupplementation: A Treatment for Osteoarthritis", J. Rheumatology, 1993, vol. 20(39):2.

Adams, "An Analysis of Clinical Studies of the Use of Crosslinked Hyaluronan, Hylan, in the Treatment of Osteoarthritis," 1993, J. Rheumatology, vol. 20(30):16-18.

Balazs et al., "Viscosupplementation: A New Concept in the Treatment of Osteoarthritis," J. Rheumatology, 1993, vol. 20(39):3-9.

Bobic, "Autologous Chondrocyte Transplantation," Am. Acad. Orthopaedic Surgeons Annual Meeting, Day 2, pp. 1-6 (2000).

Buckwalter et al., "Restoration of Injured or Degenerated Articular Cartilage," J Am. Acad. Orthopaedic Surgeons, 1994, vol. 2(4):192-201.

Kelly et al., "In Vitro Release Kinetics of Gentamycin from a Sodium Hyaluronate Gel Delivery System Suitable for the Treatment of Peripheral Vestibular Disease," Drug Dev. Indust. Pharm., 1999, vol. 25(1):15-20.

Krupla et al., "The Efficacy of Hyaluronic Acid Foam as a Middle Ear Packing Agent in Experimental Tympanoplasty," Am J. Otol., 1998, vol. 19:546-550.

Laurent et al., "Hyaluronic Acid Reduces Connective Tissue Formation in Middle Ears Filled With Absorbable Gelatin Sponge," Am. J. Otolaryogol, 1986, vol. 7(3):181-186.

Merchant et al., "Current Status and Future Challenges of Tympanoplasty," Eur. Arch. Otorhinolaryngol, 1998, vol. 255:221-228.

Miyauchi et al., "The Optimal Molecular Weight of Dispersive Type Sodium Hyaluronate for the Reduction of Corneal Endothelial Damage induced by Sonication, Irrigation, and Aspiration," Jpn J Ophthalmol., 2001, vol. 45:339-347.

Pelletier et al., "The Pathophysiology of Osteoarthritis and the Application of the Use of Hyaluronan and Hylan as Therapeutic Agents in Viscosupplementation," J. Rheumatology, 1993, vol. 20(39):19-24.

Peyron "Intraarticular Hyaluronan InjectiOns in the Treatment of Osteoarthritis: State-of-the-Art Review," J. Rheumatology, 1993, vol. 20(39):10-15.

Poyer et al., "Quantitative Method to Determine the Cohesion of Viscoelastic Agents by Dynamic Aspiration," J. Cataract Refract. Surg., 1998, vol. 24:1130-1135.

Rosiak et al., "Radiation Formation of Hydrogels for Biomedical Purposes. Some Remarks and Comments," Radiat. Phys. Chem., 1995, vol. 46(2):161-168.

Arshinoff et al., "New Classification of Ophthalmic Viscosurgical Devices—2005", J Cataract Refractive Surgery, vol. 31:2167-2171, 2005.

Praveen et al., "DisCoVisc versus the Soft-Shell Technique Using Viscoat and Provisc in Phacoemulsification: Randomized Clinical Trial", J Cataract Refractive Surgery, vol. 34:1145-1151, 2008.

* cited by examiner

COMBINATIONS OF VISCOELASTICS FOR USE DURING SURGERY

RELATED APPLICATIONS

The present application is a continuation-in-part application of U.S. patent application Ser. No. 10/381,861 filed Mar. 28, 2003, now abandoned which is a national application under 35 U.S.C. §371 of PCT Application Ser. No. PCT/US02/36548 filed Nov. 13, 2002, which draws priority from U.S. Provisional Application Ser. No. 60/342,918 filed Dec. 21, 2001, now abandoned.

FIELD OF THE INVENTION

The invention described herein relates to the field of viscosurgery and involves a novel combination of viscoelastic agents that exhibit an improved rheological profile for certain types of surgery, especially ophthalmic surgery.

BACKGROUND OF THE INVENTION

There are a number of known viscous or viscoelastic agents for ophthalmic surgical use (hereinafter "agents" or "viscoelastic agents"). For example, VISCOAT® (Alcon Laboratories, Inc.), which contains sodium hyaluronate and chondroitin sulfate; Provisc® (Alcon), Healon®, Healon® GV and Healon® 5 (Pharmacia & Upjohn), Amvisc® and Amvisc Plus® (Bausch & Lomb), and Vitrax® (Allergan), all of which contain essentially pure sodium hyaluronate (HA); and finally the hydroxypropylmethylcellulose (HPMC) products such as Cellugel® (Alcon). All of these highly purified products are useful in certain ocular surgical procedures, such as cataract surgery. They are used by the skilled ophthalmic surgeon for several surgical purposes, including maintenance of intraocular spaces, protection of ophthalmic tissues, particularly corneal endothelial cells, and as an aid in manipulating ophthalmic tissues. These agents are generally viscous enough to permit the skilled surgeon to use them for their intended surgical purposes, but not so viscous that expression of the agent through a cannula of acceptable bore size might be made difficult.

As suggested by the number of commercially available products, however, no one viscoelastic agent best fulfills all of the surgical purposes. Due to their particular physical characteristics, certain viscoelastic agents will be better suited for particular aspects of the surgical procedure. For example, in cataract surgery, the combination of relatively low molecular weight sodium hyaluronate and chondroitin sulfate found in the VISCOAT® product works well in maintaining the anterior chamber during capsulotomy, or anytime during the cataract procedure, and in adhering to and protecting tissues, particularly the corneal endothelium. However, due to its adhering and coating characteristics, the VISCOAT® product is more difficult to remove from the anterior chamber of the eye than some other agents. In addition, although it can be used to manipulate tissue for insertion of an intraocular lens (IOL) into the eye, certain other agents are better suited to perform this function.

Viscoelastic solutions of relatively high molecular weight sodium hyaluronate having functionally desirable viscosity, such as Healon® or the PROVISC® product (Alcon Laboratories, Inc.) are highly cohesive, but relatively non-adherent with respect to the tissues they may contact during surgery. These characteristics make such solutions well suited for use as a soft tool for the gentle manipulation of delicate tissues during surgery. For example, these viscoelastic agents can be used to inflate the capsular bag and facilitate the insertion of an IOL. Their cohesiveness and lack of adhering quality also make them easier to remove from the eye at the end of surgery. However, sodium hyaluronate is not as effective as some agents in protecting ophthalmic tissues, especially during phacoemulsification procedures.

HPMC adheres well to ophthalmic tissues and therefore protects them, but does not perform as well as, for example, the VISCOAT® product, in maintaining the anterior chamber, or as well as sodium hyaluronate in manipulating tissues. However, it can be easily diluted with irrigation fluid for removal following IOL implantation. The removal of the viscous or viscoelastic agent at the close of surgery is generally effected to prevent or reduce the severity of intraocular pressure spikes following surgery.

In general, viscous solutions containing relatively higher molecular weight agents, including high molecular weight sodium hyaluronate, are more effective in maintaining the intraocular space than less viscous solutions containing relatively lower molecular weight agents; however, the high molecular weight agents tend to be highly cohesive and may be prematurely aspirated from a surgical site. This may occur, for instance, if they come into contact with the aspiration port of the phacoemulsification tip during a phacoemulsification procedure. The relatively lower molecular weight products, which due to their tenacious characteristics adhere to and protect tissues, are more difficult to remove from the surgical site.

In recognition of the fact that each of the foregoing agents has certain advantages and disadvantages for a given surgical procedure, the use of multiple viscoelastic agents in a single surgical procedure has been suggested. See, U.S. Pat. No. 5,273,056. The multiple viscoelastic approach has enjoyed some commercial success. Consider, for example, Pharmacia's Healon® series—each product containing a different molecular weight fraction of sodium hyaluronate—or Alcon's DuoVisc® product, which contains both Provisc® and Viscoat®. The need remains, however, for a single viscoelastic agent that can adequately perform each of the functions associated with a given surgical procedure. The compositions of the present invention are believed to meet that need.

Commonly assigned U.S. patent application Ser. No. 09/857,543 discloses viscoelastic materials designed for use in otic surgery. Among the compositions disclosed therein is a formulation comprising 1.6% high molecular weight sodium hyaluronate and 4% chondroitin sulfate. The particular molecular weight ranges of the present invention, however, are neither disclosed nor suggested in that application, the contents of which are by this reference incorporated herein. Nor does that application suggest the unexpectedly improved performance realized by the present invention in ophthalmic surgery.

U.S. Pat. No. 6,051,560 discloses combinations of sodium hyaluronate and chondroitin sulfate for use in ophthalmic surgery. The commercial embodiment of that patent is found in the Viscoat® product, which, according to the package insert, contains 4% by weight chondroitin sulfate having a molecular weight of approximately 22,500 daltons and 3% by weight sodium hyaluronate having a molecular weight of over 500,000 daltons. As described above, the commercial product offers less than optimum performance in certain phases of the typical cataract surgical procedure. Quite unexpectedly, we have discovered that by modifying the molecular weight and concentrations of the polymeric components in the Viscoat® formulation, it is possible to create a viscoelastic agent that offers significantly improved overall performance compared to any of the products available on the market.

SUMMARY OF THE INVENTION

The present invention is directed to particular combinations of sodium hyaluronate and chondroitin sulfate, which exhibit a markedly improved rheology for performing all functions of a viscoelastic agent in an ophthalmic surgical procedure, especially a cataract procedure. During such a procedure, the unique blend of components in the viscoelastic agents of the present invention achieve satisfactory intraocular space maintenance and ocular tissue protection, and at the same time permit manipulation of ocular tissues and ease of removal at the end of the procedure. An object of the invention is to provide a single viscoelastic agent that affords the physician the functional benefits of a multiple agent system without the attendant cost and inconvenience of using multiple products/syringes during a single surgical procedure.

DETAILED DESCRIPTION OF THE INVENTION

Figure 1:
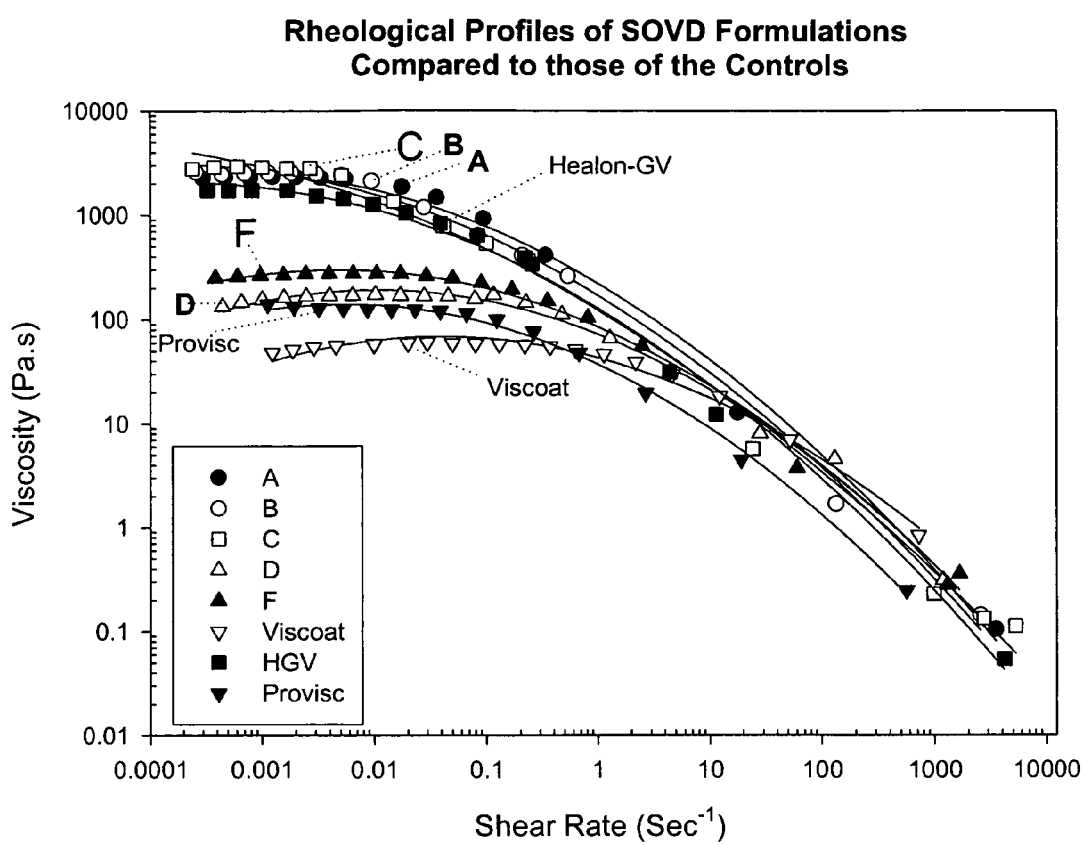
FIG. 1 is a graphic depiction of the rheological profiles of embodiments of the present invention, together with those of other viscoelastic formulations.

Viscoat® (Alcon), as discussed above, has been commercially marketed for years. The Viscoat® formulation and methods of its manufacture are generally described in U.S. Pat. No. 6,051,560, the entire contents of which are by this reference incorporated herein. Like all other stand-alone viscoelastic products currently on the market, the rheological properties of the Viscoat® material are not ideally suited for all steps of various surgical procedures, e.g. cataract surgery. The present invention is directed to new viscoelastic formulations having significantly altered rheological profiles, which permit superior performance in ophthalmic surgery, and in particular in the conventional steps or phases in the surgical removal of cataracts.

The compositions of the present invention comprise a medium molecular weight hyaluronic acid salt, preferably sodium hyaluronate, in a concentration range from about 1.0 to about 2.0% w/v in combination with chondroitin sulfate at a concentration of about 3 to about 5% w/v, in an aqueous solution suitable for ophthalmic surgery. For the hyaluronic acid/hyaluronate (HA) component, the preferred molecular weight range is about 1.5 to about 1.9 million daltons, and preferably approximately 1.7 million daltons. The preferred concentration range is from about 1.5 to about 1.8% w/v, and preferably about 1.7% w/v. For the chondroitin sulfate (CS) component, the preferred molecular weight is from about 20,000 or 25,000 to about 100,000 daltons, more preferably, from about 50,000 to about 90,000, and most preferably, about 80,000 daltons. Sodium chondroitin sulfate having molecular weight selected from the group consisting of: 20,000 daltons; 50,000 daltons; 80,000 daltons; 90,000 daltons; and 100,000 daltons is also acceptable in compositions of the present invention. The chondroitin sulfate component of the compositions of the present invention may be obtained in the desired molecular weight range from Seikagaku (Tokyo, Japan). The sodium hyaluronate component may be acquired from commercial sources such as Genzyme Corp. (Cambridge, Mass.), or prepared by means known to those skilled in the art. Molecular weight determinations of the HA component of the compositions of the present invention are weight average molecular weights as determined by gel permeation-HPLC. The compositions of the present invention may be prepared in the manner described in U.S. Pat. No. 6,051,560 previously incorporated by reference, and in the manner described in Example 1 below.

Various viscoelastic formulations comprising HA and CS were prepared in accordance with Example 1 below. These formulations were then subjected to both subjective evaluation by skilled surgeons and rheological assessment as described below.

EXAMPLE 1

Viscoelastic Preparation

A. HA raw material (sodium hyaluronate) was obtained sterile.

B. CS raw material (sodium chondroitin sulfate) was obtained non-sterile. CS was fully hydrated in buffer and sterile filtered through a 0.2µ filter.

C. Sterile HA raw material was hydrated in the sterile CS/buffer solution following an following an aseptic process while mixing in two syringes connected via a Luer-Lok connector.

D. After proper mixing and over-night hydration, a sterile clear viscous solution was obtained which was stored in refrigerator for complete de-aeration.

E. The viscous solution was then filtered through a 4.5µ filter under 50 psi pressure to yield essentially particulate-free, clear solution.

EXAMPLE 2

TABLE 1

FORMULATONS EVALUATED

| SOVD | Composition | Label |
|---|---|---|
| HMW HA | 1.6% HMWHA + 1% CS | A |
| (2.2 md) | 1.6% HMWHA + 2% CS | B |
|  | 1.6% HMWHA + 4% CS | C |
| MMW HA | 1.8% MMWHA + 1% CS | D |
| (1.6-1.8 md) | 1.8% MMWHA + 4% CS | F |
|  | 1.7% MMWHA + 4% CS | G |
| Viscoat | 3% HA + 4% CS | H |
| Healon-GV | 1.4% HMWHA | I |

HMW = high molecular weight
MMW = medium molecular weight
md = million daltons

Figure 2:
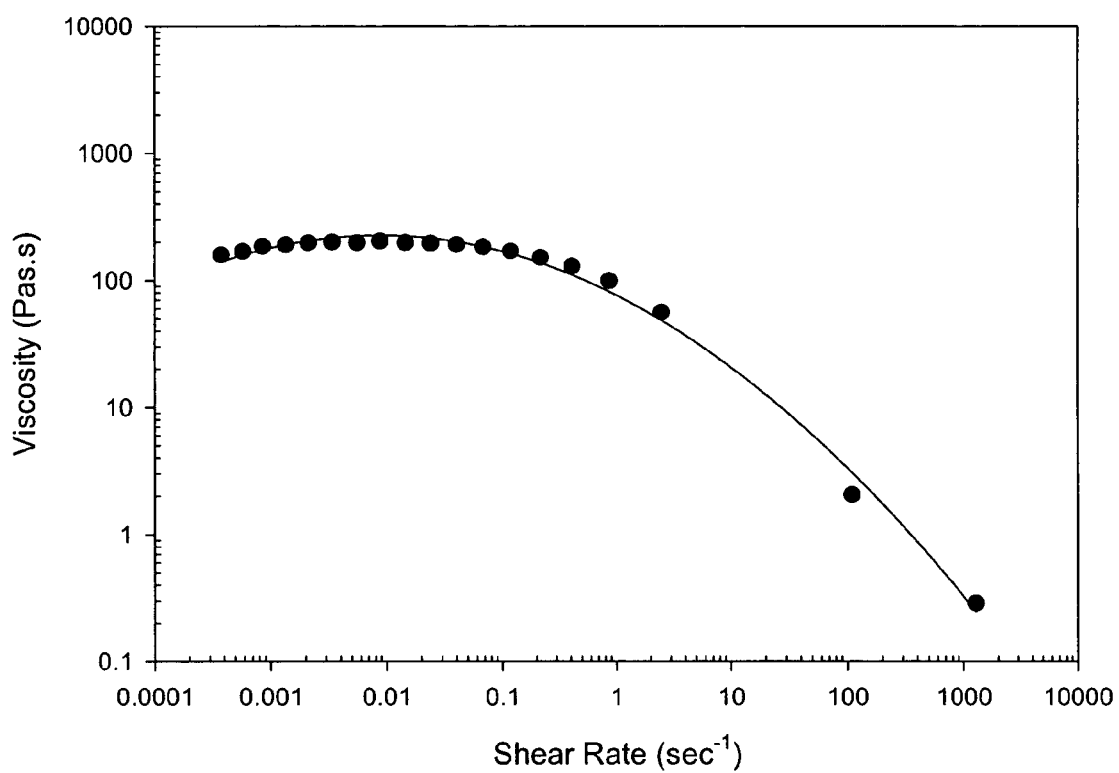
FIG. 2 is a graphic depiction of the rheological profile of a preferred embodiment of the present invention.

Rheological profiles of one preferred embodiment (Formula F) and other formulations tested, including marketed viscoelastic products, are shown in FIG. 1. From FIG. 1 it is apparent that the viscosity of Formula F falls uniquely between that of Provisc and of Healon GV at low shear rates, but surprisingly falls between that of Viscoat and of Provisc at high shear rates. A rheological profile of another preferred embodiment (Formula G) is shown in FIG. 2. As can be seen from FIG. 2, the viscosity of Formula G has similar characteristics to that of Formula F relative to the marketed viscoelastic products.

EXAMPLE 3

Table 2 presents zero shear viscosity data for the formulation G and other formulations compared to those of the marketed viscoelastic products.

TABLE 2

ZERO SHEAR VISCOSITY

| Formulation Label | Zero Shear Viscosity (Pa · s.) |
|---|---|
| A | 2300 |
| B | 2600 |
| C | 2900 |
| D | 170 |
| F | 280 |
| G | 250 |
| Viscoat | 60 |
| Provisc | 150 |
| Healon-GV | 1500 |

Consistent with the data presented in FIGS. 1 and 2, the zero shear viscosities of the medium molecular weight HA formulations of the present invention (D, F and G) are greater than the zero shear viscosities of Viscoat and Provisc, but significantly less than that of Healon-GV. Further, in terms of the Food and Drug Administration accepted viscosity measurement standard, the preferred embodiment of the present invention presented as Formula G is formulated to a viscosity of $75\pm35$ Pa·s at a shear rate of 1 sec$^{-1}$ at 25° C.

EXAMPLE 4

Several physical parameters of viscoelastic materials have been measured and are well-documented including viscosity, pseudoplasticity (shear-thinning), and molecular weight. A method to measure their cohesion is described by Poyer et al., *Quantitative method to determine the cohesion of viscoelastic agents, by dynamic aspiration, J. Cataract Refract. Surg.*, Vol. 24:1130-1135, 1998, the contents of which are by this reference incorporated herein. Poyer et al. describe a cohesion-dispersion index (CDI) for viscoelastics which is determined in a manner generally depicted in FIG. 3 and using the following materials and methods. The procedure outlined in FIG. 3 can be manually carried out or can be an automated process as will be apparent to those familiar with the art.

MATERIALS AND METHODS

Materials and Equipment

Polypropylene test tubes (found bottom, 14 mL) were obtained from Becton Dickinson Labware and polypropylene pipette tips (model RT-20), from Rainin Instrument Co. Cell culture clusters (24 well) were purchased from Costar. A Sartorius model 1612 balance was used for the gravimetric determinations and a positive displacement pipette (Rainin model M1000), for viscoelastic sample transfer. Vacuum was applied with a Gast vacuum pump.

Aspiration of Viscoelastic Sample

Figure 3:
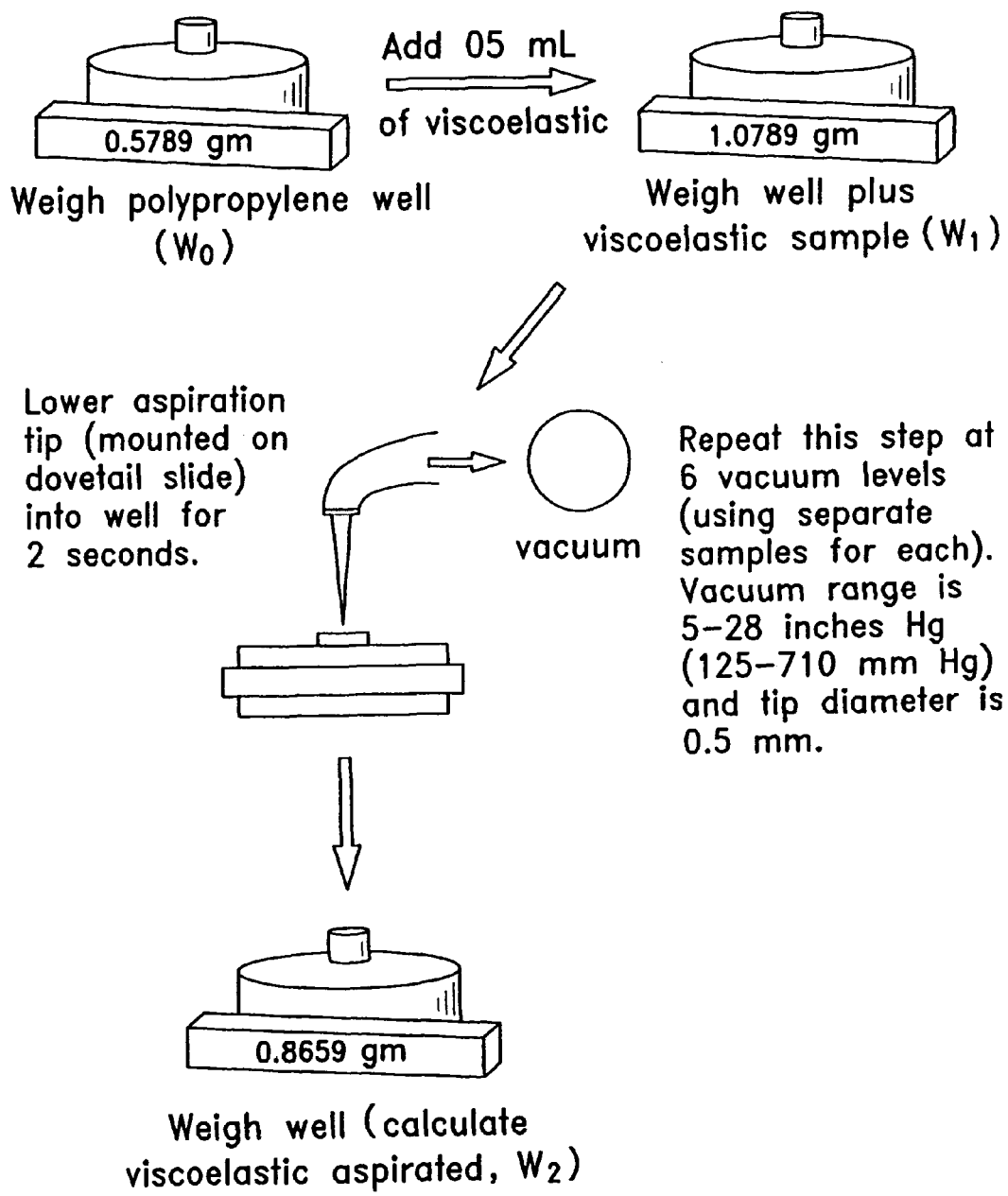
FIG. 3 is a diagram depicting a preferred method of cohesion-dispersion determination.

Polypropylene well inserts were cut from the bottom of 14 mL test tubes, weighted ($W_0$), and inserted into the well of a 24-well cell culture cluster for secure holding (FIG. 3). Polypropylene provides a non-adsorptive surface to minimize interference with aspiration by potential adsorptive forces from the container. The viscoelastic sample (0.5 mL) was dispensed into the insert with a positive displacement pipette and the insert (containing sample) reweighed ($W_1$).

A regulated vacuum was connected via flexible polyvinyl-chloride tubing to a polypropylene pipette tip (internal diameter 0.5 mm). Vacuum was applied at various levels indicated by a gauge (5, 10, 15, 20, 24, and 28 inches Hg, equivalent to 127, 254, 381, 508, 610, and 711 mm Hg) to the viscoelastic samples, using a new sample (in duplicate) for each vacuum level. Vacuum was applied with the pipette tip held in the clamp of a dovetail slide. The tip was lowered into the sample for a contact time of 2 seconds. The tip's position was fixed at an angle of 80 degrees from the horizontal surface of the sample, preventing obstruction of the tip by the bottom of the insert. After aspiration was performed for each sample, all inserts were re-weighed ($W_2$).

Data and Statistical Analysis

The percentage of the viscoelastic sample aspirated was calculated as follows:

$$\% \text{ Aspirated} = \frac{(W_1 - W_2)}{(W_1 - W_0)} \times 100\%$$

Data were plotted as percentage aspirated versus vacuum. The slopes of the steepest portion of the curve for each viscoelastic (based on the 2 steepest points of the curve) were compared for statistical significance using covariance analysis (SAS Institute, Inc.). The value of each slope represents the CDI of a particular viscoelastic agent (percentage aspirated/100 mm Hg vacuum).

The break point of a viscoelastic agent represents the vacuum level at which bolus removal of the agent begins. Bolus removal (for the purpose of break point) is defined as having more than 25% of the sample removed by a single vacuum level. Break point was determined using the percentage aspirated versus vacuum curves. Dispersive viscoelastic agents tend to have a low break point and cohesive compounds, a relatively high break point (indicative of sudden bolus removal).

The foregoing methodologies were used to determine the viscosity and CDI of the viscoelastic compositions.

TABLE 3

Cohesion-Dispersion Index (CDI)

| Product | CDI |
|---|---|
| SOVD-F Optimum | 12.3 |
| SOVD[1] (pre-eto) | 11.3, 9.0, 11.3 |
| SOVD[1] (post-eto) | 14, .3, 13.2, 15.0 |
| SOVD[2] | 11.4 |
| SOVD[2] 1.65% HA | 13.2 |
| SOVD[2] 1.7% HA | 12.8 |
| Viscoat | 3.4 |
| Provisc | 46 |
| Healon | 40 |
| Healon-GV | 72 |

[1]Heat degraded HA (sodium hyaluronate) raw material (1.6% HA).
[2]Homogenized HA (sodium hyaluronate) raw material.
The terms "pre-eto" and "post-eto" refer to before and after ethylene oxide sterilization treatment, respectively.
Unless otherwise indicated, HA concentration in the SOVD formulations is approximately 1.6%.
All concentrations are w/v.

The medium molecular weight HA formulations of the present invention (denoted SOVD in Table 3) have CDIs ranging from 9 to 15. The molecular weights of the sodium hyaluronate in these SOVD formulations range from 1.6 to 1.7 million daltons. The SOVD CDI values are significantly greater than the CDI of Viscoat, and significantly lower than the CDIs of Provisc, Healon and Healon-GV.

EXAMPLE 5

TABLE 4

EVALUATION OF PREFERRED EMBODIMENT
(Formula G)

| | |
|---|---|
| Sodium hyaluronate | 1.0-2.0% w/v |
| (medium MW: 1.5-1.9 md, preferably | preferably 1.5-1.8% w/v |
| 1.6-1.8 md) | most preferably 1.7% |
| Sodium chondroitin sulfate | 3-5% w/v |
| (MW: 20,000-100,000 daltons, preferably | preferably 4% |
| 50,000-90,000, and most preferably | |
| 80,000 daltons | |
| Monobasic sodium phosphate | 0.045% w/v |
| Dibasic sodium phosphate | 0.2% w/v |
| NaCl | 0.31% w/v |
| HCl/NaOH | To adjust pH |
| Water for Injection USP/EP | QS 100% w/v |

The preferred composition of the present invention is a viscoelastic polymer solution intended for intraocular use as a surgical aid in anterior segment surgeries. It is comprised of a medium molecular weight fraction of sodium hyaluronate (HA) at a concentration of 1.7% and sodium chondroitin sulfate (CS) with a minimum molecular weight of about 20,000 daltons at a concentration of 4% dissolved in a physiological buffer. It has an osmolality (298±32 mOsM/kg) and pH (7.2±0.4) similar to aqueous humor. The HA has an average molecular weight of 1.6 to 1.8 million daltons and was obtained from Genzyme (Cambridge, Mass.). The preferred formulation has a viscosity at rest of 200-350 Pa·s. (200,000-350,000 times higher than aqueous humor). Alternatively, viscosity of the preferred formulation (Formula G) can be expressed as 75±35 Pa·s at a shear rate of 1 $sec^{-1}$ and 25° C.

No signs of immunogenicity were reported in previous studies on HA and CS performed in humans. In a pre-clinical study in a rabbit model, this preferred embodiment was found to maintain the anterior chamber dome during phacoemulsification by remaining in the eye during phacoemulsification surgery. Proper dome maintenance is essential for effective protection of the corneal endothelium. In comparison to marketed viscoelastic products (e.g., Healon-GV and Healon-5), the composition of the embodiments of the present invention created and maintained a deeper anterior chamber during the phaco procedure, and thereby it allowed safe and controlled manipulation in the eye, with minimized trauma to the corneal endothelium and other tissues. In comparison to Viscoat, the composition of the embodiments of the present invention was easier to remove after phaco during the irrigation/aspiration (I/A) procedure, and it created and maintained a clear field of vision during surgery. The compositions of the present invention are easy to inject, as the viscosity decreases considerably when expelled through the cannula, but then immediately returns to its high viscosity state after injection. Preliminary results of pre-clinical safety indicate that the inventive composition is non-inflammatory to intraocular tissues and has an acceptable IOP profile in comparison to Healon.

Skilled practitioners will recognize that the preferred compositions of the present invention will also be particularly useful in the treatment of chondromalacia and osteoarthritis, especially grade I and grade II osteoarthritis, through intraarticular injection, as described in commonly assigned U.S. patent application Ser. No. 10/082,743, relating to the use of sodium hyaluronate and chondroitin sulfate mixtures in such therapy. The contents of said application are by this reference incorporated herein.

Those skilled in the art will similarly appreciate that the compositions and methods of the present invention will have utility in a variety of therapies and especially in drug delivery, cosmetic surgery and reconstructive surgery. The present invention is particularly well suited for delivery of anti-fibrotics, antibiotics, steroidal and non-steroidal antiinflammatories, anesthetics, analgesics and other medicaments or gene therapies to diseased or traumatized tissues in need thereof. Cosmetically, these compositions may be injected to reduce wrinkles or to treat varicose veins. For treatment of dermal lines or wrinkles, these compositions may be combined with a muscle relaxing agent such as botulinum toxin type A, commercially available as BOTOX® (Allergan, Inc., Irvine Calif., USA), and injected subdermally in the conventional manner. The presently disclosed compositions and methods may also be used in any environment where there is a need for tissue separation or stabilization and the potential exists for complications, typically post-surgical, arising from tissue fibrosis and/or adhesions. They will be particularly useful in nasal, spinal cord, cardiovascular, orthopoedic and orthodontic surgical procedures that would otherwise be prone to such complications. Skilled practitioners will recognize that the preferred retention characteristics of the viscoelastic agent will depend upon the type of procedure for which it is being employed.

As used herein, the term "ophthalmically acceptable," when used to describe salts or vehicles, means any salt or vehicle that would be suitable for administration to the eye of a patient by any conventional means, and particularly during surgery, without significant risk of deleterious health consequences. Sodium salts of hyaluronic acid and chondroitin sulfate, and aqueous vehicles are most preferred.

The present invention has been described by reference to certain preferred embodiments; however, it should be understood that it may be embodied in other specific forms or variations thereof without departing from its spirit or central characteristics. The embodiments described above are therefore considered to be illustrative in all respects and not restrictive, the scope of the invention being indicated by the appended claims rather than by the foregoing description.

What is claimed is:

1. A sterile, aqueous viscoelastic composition for use in ophthalmic surgical procedures, comprising a combination of hyaluronic acid and chondroitin sulfate, or ophthalmically acceptable salts thereof, in an ophthalmically acceptable vehicle, wherein the hyaluronic acid or ophthalmically acceptable salt thereof has a molecular weight of 1,600,000 to 1,800,000 daltons and is present at a concentration of 1.5% to 1.8% w/v; and wherein the chondroitin sulfate or ophthalmically acceptable salt thereof has a molecular weight of 20,000 to 100,000 daltons and is present at a concentration of 3% to 5% w/v, and the composition has a cohesion-dispersion index of 9 to 15 and a zero shear viscosity of 200 to 350 Pa·s.

2. The composition of claim 1, wherein the hyaluronic acid or ophthalmically acceptable salt thereof comprises sodium hyaluronate at a concentration of 1.7% w/v.

3. The composition of claim 2, wherein the sodium hyaluronate has a molecular weight of 1,700,000 daltons.

4. The composition of claim 3, wherein the chondroitin sulfate or ophthalmically acceptable salt thereof is present at a concentration of 4% w/v.

5. The composition of claim 1, wherein the composition further comprises:

| | |
|---|---|
| monobasic sodium phosphate at | 0.045% w/v; |
| dibasic sodium phosphate at | 0.2% w/v; and |
| NaCl at | 0.31% w/v. |

6. The composition of claim 1, wherein the chondroitin sulfate or ophthalmically acceptable salt thereof is sodium chondroitin sulfate having a molecular weight selected from the group consisting of: 20,000 daltons; 50,000 daltons; 80,000 daltons; 90,000 daltons; and 100,000 daltons.

7. A method of performing cataract surgery on an eye, comprising administering to the eye a tissue stabilizing effective amount of a sterile, aqueous viscoelastic composition for use in ophthalmic surgical procedures, wherein the viscoelastic composition comprises a combination of hyaluronic acid and chondroitin sulfate, or ophthalmically acceptable salts thereof, in an ophthalmically acceptable vehicle, wherein the hyaluronic acid or ophthalmically acceptable salt thereof has a molecular weight of 1,600,000 to 1,800,000 daltons and is present at a concentration of 1.5 to 1.8% w/v; and wherein the chondroitin sulfate or ophthalmically acceptable salt thereof has a molecular weight of 20,000 to 100,000 daltons and is present at a concentration of 3% to 5% w/v, and the composition has a cohesion-dispersion index of 9 to 15 and a zero shear viscosity of 200 to 350 Pa·s.

8. The method of claim 7, wherein the hyaluronic acid or ophthalmically acceptable salt thereof comprises sodium hyaluronate at a concentration of 1.7% w/v.

9. The method of claim 8, wherein the sodium hyaluronate has a molecular weight of 1,700,000 daltons.

10. The method of claim 9, wherein the chondroitin sulfate or ophthalmically acceptable salt thereof is present at a concentration of 4% w/v.

11. The method of claim 7, wherein the viscoelastic composition further comprises:

| | |
|---|---|
| monobasic sodium phosphate at | 0.045% w/v; |
| dibasic sodium phosphate at | 0.2% w/v; and |
| NaCl at | 0.31% w/v. |

12. The method of claim 7, wherein the chondroitin sulfate or ophthalmically acceptable salt thereof is sodium chondroitin sulfate having a molecular weight selected from the group consisting of: 20,000 daltons; 50,000 daltons; 80,000 daltons; 90,000 daltons; and 100,000 daltons.

13. A sterile, aqueous viscoelastic composition for use in ophthalmic surgical procedures, comprising a combination of hyaluronic acid and chondroitin sulfate, or ophthalmically acceptable salts thereof, in an ophthalmically acceptable vehicle, wherein the hyaluronic acid or ophthalmically acceptable salt thereof has a molecular weight of 1,700,000 daltons and is present at a concentration of 1.7% w/v; and wherein the chondroitin sulfate or ophthalmically acceptable salt thereof has a molecular weight of 20,000 to 100,000 daltons and is present at a concentration of 4% w/v, and wherein the composition has a cohesion-dispersion index of 9 to 15 and a zero shear viscosity of 200 to 350 Pa·s.

* * * * *